United States Patent [19]

Hamann

[11] 4,205,669
[45] Jun. 3, 1980

[54] DIAPER-CHANGING AID

[76] Inventor: Asta M. Hamann, Parkfield School Rte., San Miguel, Calif. 93451

[21] Appl. No.: 948,084

[22] Filed: Oct. 2, 1978

[51] Int. Cl.$^2$ ............................................. A61F 13/00
[52] U.S. Cl. ..................................... 128/134; 269/328
[58] Field of Search ................ 128/133, 134; 269/328; 5/100

[56] References Cited

U.S. PATENT DOCUMENTS

| | | | |
|---|---|---|---|
| 2,252,357 | 8/1941 | Shaw | 128/134 |
| 2,594,883 | 4/1952 | Donnen | 128/134 |
| 2,631,301 | 3/1953 | Hyland | 128/134 |
| 2,846,700 | 8/1958 | DePuy | 269/328 |
| 3,034,502 | 5/1962 | Lind | 128/134 |
| 3,306,287 | 2/1967 | Arp | 128/134 |
| 3,721,434 | 3/1973 | Spies | 269/328 |

*Primary Examiner*—Lawrence W. Trapp
*Attorney, Agent, or Firm*—Lawrence Fleming

[57] ABSTRACT

A diaper-changing aid for infants or retarded children, comprising a base which supports a vertical barrier of mesh, netting or other soft yieldable material which extends across the baby's chest. The barrier keeps the baby's hands out of the way and occupied. It is preferably stretched across an arch-shaped frame, with elastic fastened along the middle portion of the lower edge of the netting. One side of the arch is pivoted or hinged to the base, so that it can be swung up. The baby is then laid down on the base and the arch swung down and its opposite end fastened down by a suitable catch device. The elastic extends across the baby's chest. The diapering process may then proceed on the lower side of the barrier. Toys may be hung from the arch. Adjustable ankle straps may be provided at the lower portion of the base. The base may be made of a solid sheet of composition board or the like with padding on top. Alternatively it may be of skeleton construction with a pair of longitudinal rails or bars connected by a cross member at the chord of the arch. These members may be made of metal strip. The device is also usable for cleaning, medication, and the like.

12 Claims, 7 Drawing Figures

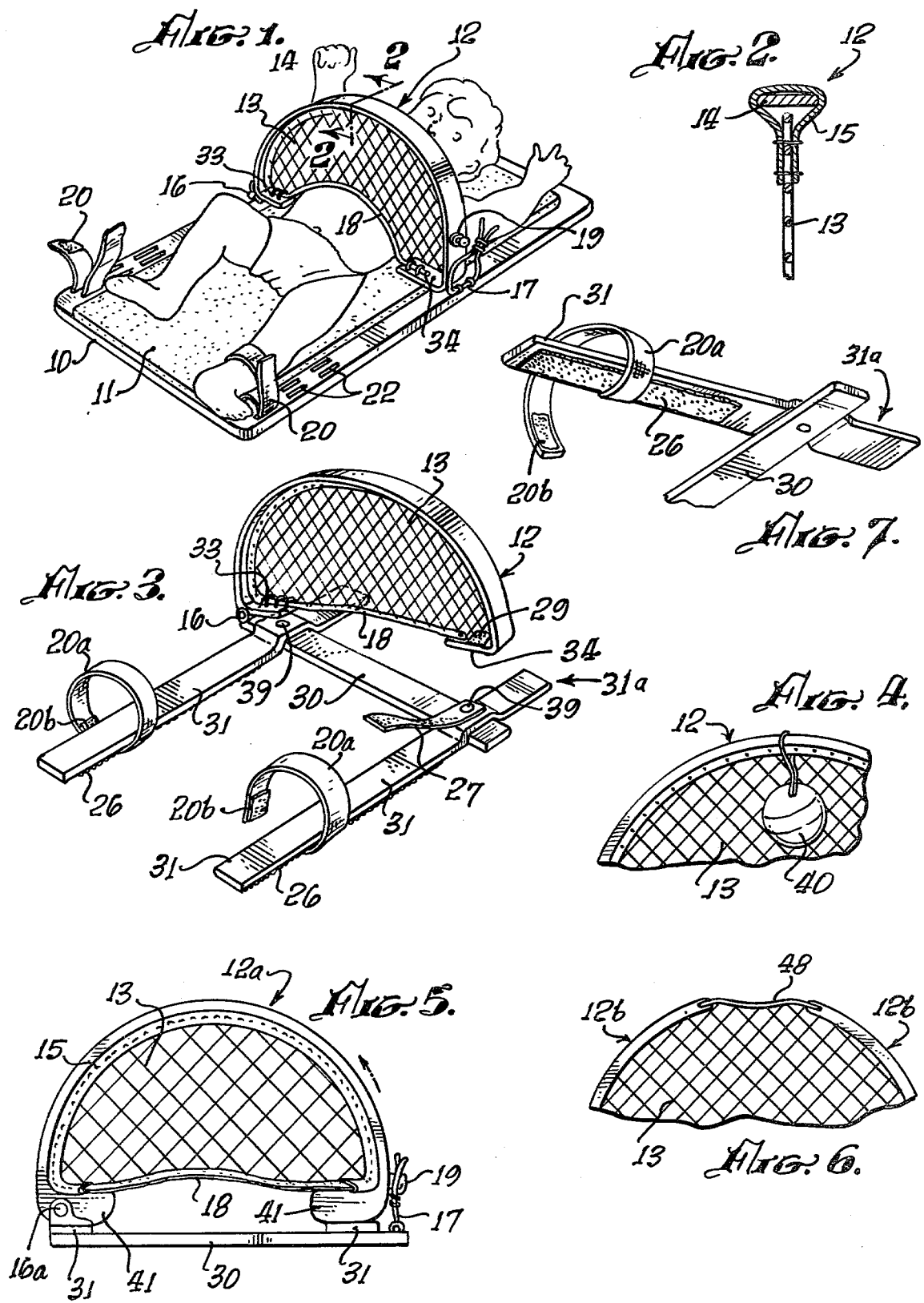

DIAPER-CHANGING AID

BACKGROUND

In diapering, cleaning, or applying medication to an infant it is desirable to keep the baby from grabbing at things as well as to keep it from rolling off the table. Bassinets are often provided with chest straps for the latter purpose. The only prior devices for controlling the baby's hands appear, however, to be straps; and these may lead to undesirable struggling. There is a need for a suitable device that serves both purposes while keeping the baby occupied, amused, and relaxed. Preferably the device (unlike an ordinary bassinet) is made portable, as for convenience while traveling.

SUMMARY

An arch-like frame extends across a base on which the baby is laid. Mesh, netting, or other soft flexible material is fastened across the frame to form a barrier. The bottom edge of the barrier contains a length of elastic, which is fastened across the ends of a pair of inward extensions of the chordal base portion of the arch or frame. The elastic is disposed so as to pass over the baby's chest under a little tension.

The barrier is hinged at one side so that it can be swung up out of the way. The baby may then be laid on the base or table and the barrier swung back down. Opposite the hinge end is a suitable catch or fastener to hold the barrier down.

The base may be a suitable rectangle of composition board, plywood, or the like, e.g., about 45 by 82 cm and 6 mm thick, with the barrier about 30 cm from the head end. A suitable soft pad or mat may be fastened over its top. Ankle straps are preferably provided near the outer edges of the foot end portion of the base, to keep the baby from rolling over. The strap position is preferably adjustable for babies of different lengths.

A modified base is of skeleton construction. A cross-member extends across below the lower chordal portion of the arch or frame; the hinge and catch are near its ends. Also fastened near the ends of the cross-member is a pair of longitudinal rails or bars. The bars and cross-member may be made of aluminum strip or the like, and the bars made detachable for shipping. This modification is for use on a bed or a table top. Anchoring strips of hook pile material (such as sold under the trade name "Velcro") may be fastened along the undersides of the bars. The ankle straps, fitted with mating loop pile material, may then be fastened to the anchoring strips at desired points along their length, for adjustability.

In another modification the arch may be open at the top, with the gap bridged with a length of cord or elastic. In another modification the arch may be of molded plastic, composition, or wood with thickened lower inward extension portions which provide abutments at either side of the baby to help prevent him from rolling to one side or the other.

The device is also useful for cleaning infants, applying ointments or other topical medication, and for facilitating medical treatment. It may be scaled in size for use with, e.g., mentally retarded children.

DETAILED DESCRIPTION

In the drawing:

FIG. 1 is a perspective view of one form of the invention;

FIG. 2 is a sectional detail view on line 2—2 of FIG. 1;

FIG. 3 is a perspective view of a modification;

FIG. 4 is an end view of a modified detail;

FIG. 5 is an end view of another modification of the complete device;

FIG. 6 is an end view of another modified detail; and

FIG. 7 is a bottom perspective detail of FIG. 3.

Referring first to FIG. 1, a flat base of suitable composition board material, plywood, or the like is shown at 10, with a suitable pad or cushion on top at 11. An arch-like barrier is mounted across the base 10, nearer the head end than the foot end, to extend across the baby's chest region. It is covered with mesh or netting 13 or other flexible fabric or like material to provide a yieldable soft barrier 12, which is preferably transparent in the sense that one can see objects through it, e.g., of open construction. The mesh is chosen preferably so that the baby's fingers may pass through the openings, but not the baby's hands. It is found that such a barrier provides a form of confinement without instilling fear, and a form of occupation for the infant's hands. Toys may be fastened to the top of the barrier.

The netting 13 may be secured around an arch-like frame 14 by a suitable fabric or plastic binding 15 (FIG. 2), to form barrier 12.

The bottom of the frame member 14 of barrier 12, FIG. 1, is preferably extended horizontally inward as at 33, 34, FIG. 1. Fastened between these inward chordal extended portions is a length 18 of stretchable elastic cord, ribbon, or the like such as is used in making clothing. All or a portion of the bottom edge of netting 13 is secured along the elastic 18 by any suitable means.

Referring again to the detail section of FIG. 2, the frame 14 of the barrier 12 may be made from a suitable length of flat metal stock such as aluminum or steel strip. Here, the binding is shown at 15, into which the upper perimeter portion of the netting 13 is fastened as by sewing, by glue, or by heat sealing or other means.

Returning to FIG. 1, one side of barrier 12 is hinged at 16 to base 10 so that it can be tilted up. On the other side of barrier 12 is a suitable detachable fastener or catch to hold it down; this may be an elastic loop 17 which hooks over a button 19, or other suitable means.

To use the device, the barrier 12 is tilted up and the baby placed on the base 10, 11. The barrier is then brought down and fastened at 17. The elastic 18 has now been stretched gently over the baby's chest, his hands and arms being behind the barrier 12. The diapers may then be changed with a minimum of interference from the baby, who, however, can see the operation and has something to occupy his hands.

Ankle straps 20, 20 are provided to keep the baby from turning over. These may be fabric or flexible plastic strips with suitable patches of hook-and-loop pile material for fastening their ends together. Such material is sold under the trade name "Velcro". Straps 20 may be secured to base 10 by passing them up and down through pairs of slots 22. Several pairs of slots 22 are preferably provided to accommodate babies of different lengths.

FIG. 3 shows a modification with a skeletonized base 30, 31 for use on a bed, table top, or other suitable support surface. A towel may be laid over the base members before the baby is laid down. The barrier 12 is hinged at 16 to a cross-member 30. Generally-longitudinal rails or bars 31, 31 are fastened to the end portions of cross-member 30 as by screws or rivets 39. The rails 31 may be parallel as shown or nonparallel, and may be shorter at the head end, as at 31a, since other support (the bed or table top) is available under the baby's head. A detachable fastener or catch means is provided as before to hold the barrier down. This may preferably take the form of a strip 27 of loop pile material fastened at one end to a screw or rivet 39, which is passed over a mating patch of hook pile material 29 on frame portion 34.

The cross member 30 and bars 31 may be of flat metal strip or other suitable material. Bars 31 may be detachable from member 30 as by screws at 39, to permit disassembly for shipping.

In FIGS. 3 and 7, the ankle straps 20a, 20a preferably attached to anchoring strips 26, 26 of hook pile material ("Velcro" or the like) which are glued or otherwise secured along the undersides of the longitudinal rails or bars 31, 31. The straps 20a are preferably of elastic with patches of mating hook pile material at their ends. The straps may thus be fastened at various points along the anchoring strips 26, depending on the length of the baby.

FIG. 5 shows a device with a modified barrier in end view. Base cross member 30 and bars 31 may be made as in FIG. 3, or alternatively a flat solid base of the FIG. 1 type may be used. The modified barrier 12a has thickened portions at its base which terminate in abutments 41, 41. The baby lies between these abutments, and so is additionally restrained and protected from rolling. Elastic 18 fits over the baby's chest as before. The modified arch or frame 14a may be made of wood or of a moldable plastic or composition material suited to its general shape.

FIG. 6 shows a modified barrier with a frame made of two curved halves 12b, 12b with a gap between them at the top. The gap is bridged by a length of cord or elastic 48 to which the corresponding edge portion of net 13 is fastened. This barrier is foldable when disassembled from the base.

The device may be used to hold an infant for medical examination or treatment as well as for diapering. It may be scaled to a larger size for use with, e.g., retarded children. The barrier 12 may be given a different shape from the generally semicircular shape shown, such as rectangular; and the frame members 14, 30, 31 may be made of wood, or of metal channel or angle stock, or of round or square tubing, within the purview of the invention. The barrier covering at 13 may be made of string or thread like a fish net, or of expanded plastic netting in known manner, or be of woven fabric. The hinge means such as 16 may be of flexible strips, pins fitting in holes, or any other known means that permits the barrier 12 to be tilted up.

Instead of hinge means such as 16 at one end of the barrier 12, other known means may be provided to get the barrier out of the way when the baby is being laid down or removed. For example, the barrier as a whole may be made removable as by plug-in or other detachable fastening means at both ends.

I claim:

1. A diaper-changing, cleaning, and medication aid for a baby or the like, comprising:
 a generally horizontal base having a head end, a foot end, and sides,
 said base being adapted to be disposed under a baby lying on its back; and
 a generally vertical barrier extending across said base and having a lower edge portion disposed to extend substantially across the chest region of said baby.

2. The structure of claim 1, wherein:
 said barrier comprises a frame portion and an inner barrier portion attached thereto and made of soft yieldable sheet-like material.

3. The structure of claim 1, wherein:
 said barrier comprises a generally arch-shaped frame portion with said sheet-like material fastened across it,
 a central portion of the lower chordal edge of said netting being attached to a length of elastic material adapted to pass over the said baby's chest.

4. The structure of claim 3, further comprising:
 hinge means connecting one end of said arch-shaped frame portion to a said side of said base, and
 a barrier catch connecting the opposite side of said arch to the opposite side portion of said base,
 whereby said barrier may be swung up to clear said base and then swung back down over said baby.

5. The structure of claim 4, further comprising:
 inner extensions of said arch-like frame portion extending inward along a portion of the chord thereof about in the plane of said base and leaving a lower gap,
 said elastic being attached across said extensions and bridging said lower gap.

6. The structure of claim 4, wherein:
 said base comprises generally a rectangle of substantially rigid sheet material,
 and further comprising:
 slots in said base and ankle straps passing through said slots and adapted to fasten detachably around the ankles of said baby.

7. The structure of claim 4, wherein:
 said base is a skeletonized structure comprising a cross-member and a pair of longitudinal bar members,
 said bar members being fastened to the end portions of said cross-member, and
 said hinge means and said barrier catch being mounted at the end portions of said cross-member.

8. The structure of claim 7, further comprising:
 an anchoring strip of loop pile material extending along the underside of each said bar member, and
 a pair of ankle straps of elastic with mating hook pile material thereon adapted to detachably engage said anchoring strips at any point along their length,
 whereby each said ankle strap may be fastened at a selected distance below said barrier.

9. The structure of claim 5, wherein:
 said inner extensions of said arch-like frame portion are of substantial vertical thickness, their generally-vertical inner end portions providing abutment-like side support for said baby.

10. The structure of claim 4, wherein:
 said arch-like frame portion is partially open at the top to provide a top gap,
 and further comprising:
 a length of flexible material bridging said gap.

11. The structure of claim 4, further comprising:
 means to fasten toys to the upper portion of said barrier.

12. The structure of claim 3, wherein said sheet-like material is netting.

* * * * *